(12) United States Patent
Zuker

(10) Patent No.: US 7,335,479 B2
(45) Date of Patent: *Feb. 26, 2008

(54) ASSAYS FOR SENSORY MODULATORS USING A SENSORY CELL SPECIFIC G-PROTEIN ALPHA SUBUNIT

(75) Inventor: Charles S. Zuker, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 139 days.

This patent is subject to a terminal disclaimer.

(21) Appl. No.: 11/084,627

(22) Filed: Mar. 18, 2005

(65) Prior Publication Data

US 2005/0164310 A1 Jul. 28, 2005

Related U.S. Application Data

(62) Division of application No. 09/492,028, filed on Jan. 26, 2000, now Pat. No. 6,875,574.

(60) Provisional application No. 60/117,367, filed on Jan. 27, 1999.

(51) Int. Cl.
   G01N 33/53 (2006.01)
   G01N 33/566 (2006.01)
   C12P 21/02 (2006.01)
   C12Q 1/00 (2006.01)
   C07K 14/47 (2006.01)

(52) U.S. Cl. .................. 435/7.1; 435/4; 435/7.2; 435/69.1; 436/501; 530/300; 530/350

(58) Field of Classification Search ................ None
See application file for complete search history.

(56) References Cited

U.S. PATENT DOCUMENTS 6,008,000 A 12/1999 Margolskee et al.
6,383,778 B1 5/2002 Zuker et al.

FOREIGN PATENT DOCUMENTS

WO WO 00/44929 8/2000

OTHER PUBLICATIONS

Hohenegger et al. Gs-alpha-selective G protein antagonists. Proc Natl Acad Sci USA 95:346-351, 1998.*
Cheung et al. Specific activation of Gs by synthetic peptides corresponding to an intracellular loop of the beta-adrenergic receptor. FEBS Letters 279(2): 277-280, 1991.*
Freissmuth et al. Suramin analogues as subtype-selective G protein inhibitors. Mol Pharmacol 49: 602-611, 1996.*
Hepler et al. RGS4 and GAIP are GTPase-activating proteins for Gq-alpha and block activation of phospholipase C-beta by gamma-thio-GTP-Gq-alpha. Proc Natl Acad Sci USA 94: 428-432, 1997.*
Strathmann et al. G protein diversity: a distinct class of alpha subunits is present in vertebrates and invertebrates. Proc Natl Acad Aci USA 87: 9113-9117, 1990.*
Offermanns et al. G-alpha-q family members couple parathyroid hormone (PTH)/PTH-related peptide and calcitonin receptors to phospholipase C in COS-7 cells. Mol Endocrin 10: 566-574, 1996.*
Shapira et al. G-alpha14 and G-alpha-q mediate the response to trypsin in Xenopus oocytes. J Biol Chem 273(31): 19431-19436, 1998.*
Offermanns et al. Gα15 and Gα16 couple a wide variety of receptors to phospholipase C. J Biol Chem 270(25): 15175-15180, 1995.*
Adler et al.: "A novel family of mammalian taste receptors," *Cell*, vol. 100; pp. 693-702 (2000).
Bork, A.: "Powers and pitfalls in sequence analysis: the 70% hurdle," *Genome Res.*, vol. 10; pp. 398-400 (2000).
Bork, et al.: "Go hunting in sequence databases but watch out for the traps," *Trends in Genetics*, vol. 12, No. 10; pp. 425-427 (1996).
Brenner, S. E.: "Errors in genome function," *Trends in Genetics*, vol. 15, No. 4; pp. 132-133 (1999).
Chandrashekar, J. et al.: "T2Rs function as bitter taste receptors," *Cell*, vol. 100; pp. 703-711 (2000).
Doerks, et al.: "Protein annotation: detective work for function prediction," *Trends in Genetics*, vol. 16, No. 6; pp. 248-250 (1998).
Hoon, et al.: "Putative Mammalian Taste Receptors: A Class of Taste-Specific GPCRs with Distinct Topographic Selectivity," *Cell*; vol. 96, pp. 541-551 (1999).
Hoon, M.A. and N.J.P. Ryba: "Analysis and Comparison of Partial Sequences of Clones from a Taste-bud-enriched cDNA Library," *J. Dent Res*; vol. 76, No. 4, pp. 831-838 (1997).
Kinnamon, S. C. and R. F. Margolskee: "Mechanisms of taste transduction," *Neurobology*, vol. 6, pp. 506-513 (1996).
Kusakabe, et. al.: "Identification of two α-subunit species of GTP-binding proteins, Gα15 and Gαq, expressed in rat taste buds," *Biochimica et Biophysica Acta*; vol. 1403, pp. 265-272; (1998).
Matsunami et al., "A family of candidate taste receptors in human and mouse," *Nature*, vol. 404; pp. 601-604 (2000).
Mclauglin, et.al: "Gustducin is a taste-cell specific G protein closely related to the transducins," *Nature*; vol. 357; pp. pp. 563-569 (1992).
Mombaerts, P.: "Seve-transmembrane proteins as odorant and chemosensory receptors," Science, vol. 286, pp. 707-711 (1999).
Nelson, G. et al.: "An amino-acid taste receptor," *Nature*, vol. 416, pp. 199-202 (2002).
Nelson, G. et al.: "Mammalian sweet taste receptors," *Cell*, vol. 106; pp. 381-390 (2001).
Ngo, et al.: "Computational complexity, protein structure prediction, and the Levinthal paradox." in The Protein Folding Problem and Tertiary Structure Prediction, by K. M. Merz, Jr. and S. M. Le Grand (eds.), Birkhauser Boston; at pp. 492-495 (1994).

(Continued)

Primary Examiner—Bridget E. Bunner
(74) Attorney, Agent, or Firm—Townsend and Townsend and Crew LLP

(57) ABSTRACT

The invention identifies nucleic acid and amino acid sequences of a sensory cell specific G-protein alpha subunit that are specifically expressed in sensory cells, e.g., taste cells, antibodies to such G-protein alpha subunits, methods of detecting such nucleic acids and subunits, and methods of screening for modulators of a sensory cell specific G-protein alpha subunit.

13 Claims, No Drawings

OTHER PUBLICATIONS

Skolnick et al.: "From genes to protein structure and function: novel applications of computational approaches in the genomic era," *Trends in Biotech.*, vol. 18, No. 1; pp. 34-39 (2000).

Smith, et al.: "The challenges of genome annotation or 'The devil is in the details'," *Nature Biotech.*, vol. 15; pp. 1222-1223 (1997).

Striem, et. al.: "Sweet tastants stimulate adenylate cyclase coupled to GTP-binding protein in rat tongue membranes," *Biochem J.*; vol. 260, pp. 121-126 (1989).

Takami et al.: "Human taste cells express the G protein alpha-gustducin and neuron-specific enolase," *Molec. Brain Res.*, vol. 22; pp. 193-203 (1994).

Wells, J.A.: "Additivity of mutational effects in proteins," *Biochemistry*, vol. 29, No. 37; pp. 8509-8517 (1990).

Wilke, et. al: "Characterzation of G-protein $\alpha$ subunits in the $G_\alpha$ class: Expression in murine tissues and in stromal and hematopoietic cell lines," *Proc. Natl. Acad. Sci. USA*; vol. 88, pp. 10049-10053 (1991).

Wong, et. al.: "Transduction of bitter and sweet taste by gustducin" *Nature*; vol. 381; pp. 796-800 (1998).

* cited by examiner

ASSAYS FOR SENSORY MODULATORS USING A SENSORY CELL SPECIFIC G-PROTEIN ALPHA SUBUNIT

CROSS-REFERENCES TO RELATED APPLICATIONS

This application is a divisional of U.S. patent application Ser. No. 09/492,028, filed Jan. 26, 2000, now U.S. Pat. No. 6,875,574, which claims priority to U.S. Provisional Patent Application Ser. No. 60/117,367, filed Jan. 27, 1999, herein incorporated by reference in its entirety.

STATEMENTS AS TO RIGHTS TO INVENTIONS MADE UNDER FEDERALLY SPONSORED RESEARCH AND DEVELOPMENT

This invention was made with Government support under Grant No. DC03160, awarded by the National Institutes of Health. The Government has certain rights in this invention.

FIELD OF THE INVENTION

The invention identifies nucleic acid and amino acid sequences of a taste cell specific G-protein alpha subunit that are specifically expressed in taste cells, antibodies to such G-protein alpha subunits, methods of detecting such nucleic acids and subunits, and methods of screening for modulators of taste cell specific G-protein alpha subunit.

BACKGROUND OF THE INVENTION

Taste transduction is one of the most sophisticated forms of chemotransduction in animals (see, e.g., Avenet & Lindemann, *J. Membrane Biol.* 112:1-8 (1989); Margolskee, *BioEssays* 15:645-650 (1993)). Gustatory signaling is found throughout the animal kingdom, from simple metazoans to the most complex of vertebrates; its main purpose is to provide a reliable signaling response to non-volatile ligands. Higher organisms have four basic types of taste modalities: salty, sour, sweet, and bitter. Each of these modalities is thought to be mediated by distinct signaling pathways leading to receptor cell depolarization, generation of a receptor or action potential, and the release of neurotransmitter and synaptic activity (see, e.g., Roper, *Ann. Rev. Neurosci.* 12:329-353 (1989)).

Mammals are believed to have five basic taste modalities: sweet, bitter, sour, salty and unami (the taste of monosodium glutamate) (see, e.g., Kawamura & Kare, *Introduction to Umami: A Basic Taste* (1987); Kinnamon & Cummings, *Ann. Rev. Physiol.* 54:715-731(1992); Lindemann, *Physiol. Rev.* 76:718-766 (1996); Stewart et al., *Am. J. Physiol.* 272:1-26 (1997)). Extensive psychophysical studies in humans have reported that different regions of the tongue display different gustatory preferences (see, e.g., Hoffmann, *Menchen. Arch. Path. Anat. Physiol.* 62:516-530 (1875); Bradley et al., *Anatomical Record* 212:246-249 (1985); Miller & Reedy, *Physiol. Behav.* 47:1213-1219 (1990)). Also, numerous physiological studies in animals have shown that taste receptor cells may selectively respond to different tastants (see, e.g., Akabas et al., *Science* 242:1047-1050 (1988); Gilbertson et al., *J. Gen. Physiol.* 100:803-24 (1992); Bernhardt et al., *J. Physiol.* 490:325-336 (1996); Cummings et al., *J. Neurophysiol.* 75:1256-1263 (1996)). In mammals, taste receptor cells are assembled into taste buds that are distributed into different papillae in the tongue epithelium. Circumvallate papillae, found at the very back of the tongue, contain hundreds (mice) to thousands (human) of taste buds and are particularly sensitive to bitter substances. Foliate papillae, localized to the posterior lateral edge of the tongue, contain dozens to hundreds of taste buds and are particularly sensitive to sour and bitter substances. Fungiform papillae containing a single or a few taste buds are at the front of the tongue and are thought to mediate much of the sweet taste modality.

Each taste bud, depending on the species, contain 50-150 cells, including precursor cells, support cells, and taste receptor cells (see, e.g., Lindemann, *Physiol. Rev.* 76:718-766 (1996)). Receptor cells are innervated at their base by afferent nerve endings that transmit information to the taste centers of the cortex through synapses in the brain stem and thalamus. Elucidating the mechanisms of taste cell signaling and information processing are critical for understanding the function, regulation, and "perception" of the sense of taste.

Although much is known about the psychophysics and physiology of taste cell function, very little is known about the molecules and pathways that mediate these sensory signaling responses (reviewed by Gilbertson, *Current Opn. in Neurobiol.* 3:532-539 (1993); see also McLaughlin et al., *Nature* 357:563-568 (1992)). Electrophysiological studies suggest that sour and salty tastants modulate taste cell function by direct entry of $H^+$ and $Na^+$ ions through specialized membrane channels on the apical surface of the cell. In the case of sour compounds, taste cell depolarization is hypothesized to result from $H^+$ blockage of $K^+$ channels (see, e.g., Kinnamon et al., *PNAS USA* 85:7023-7027 (1988)) or activation of pH-sensitive channels (see, e.g., Gilbertson et al., *J. Gen. Physiol.* 100:803-24 (1992)); salt transduction may be partly mediated by the entry of $Na^+$ via amiloride-sensitive $Na^+$ channels (see, e.g., Heck et al., *Science* 223:403-405 (1984); Brand et al, *Brain Res.* 207-214 (1985); Avenet et al., *Nature* 331:351-354 (1988)). Most of molecular components of the sour or salty pathways have not been identified.

Sweet, bitter, and unami transduction are believed to be mediated by G-protein-coupled receptor (GPCR) signaling pathways (see, e.g., Striem et al., *Biochem. J.* 260:121-126 (1989); Chaudhari et al., *J. Neuros.* 16:3817-3826 (1996); Wong et al., *Nature* 381:796-800 (1996)). Confusingly, there are almost as many models of signaling pathways for sweet and bitter transduction as there are effector enzymes for GPCR cascades (e.g., G protein subunits, cGMP phosphodiesterase, phospholipase C, adenylate cyclase; see, e.g., Kinnamon & Margolskee, *Curr. Opin. Neurobiol.* 6:506-513 (1996)). Identification of molecules involved in taste signaling is important given the numerous pharmacological and food industry applications for bitter antagonists, sweet agonists, and modulators of salty and sour taste.

The identification and isolation of taste receptors (including taste ion channels), and taste signaling molecules, such as G-protein subunits and enzymes involved in signal transduction, would allow for the pharmacological and genetic modulation of taste transduction pathways. For example, availability of receptor, ion channels, and other molecules involved in taste transduction would permit the screening for high affinity agonists, antagonists, inverse agonists, and modulators of taste cell activity. Such taste modulating compounds could then be used in the pharmaceutical and food industries to customize taste. In addition, such taste cell specific molecules can serve as invaluable tools in the generation of taste topographic maps that elucidate the relationship between the taste cells of the tongue and taste sensory neurons leading to taste centers in the brain.

SUMMARY OF THE INVENTION

The present invention demonstrates, for the first time, taste receptor cell specific expression of nucleic acids encoding G-protein alpha subunit. Specifically, the present invention identifies that G14, a G-protein alpha subunit, is specifically and selectively expressed in taste receptor cells. This gene was found to be co-expressed with G-protein coupled taste receptors, GPCR-B3 and GPCR-B4 (see U.S. Ser. No. 09/361,652, filed Jul. 27, 1999 and U.S. Ser. No. 09/361,631, filed Jul. 27, 1999, now U.S. Pat. No. 6,383, 778). Functionally, GPCR-B3 and GPCR-B4 each represents a seven transmembrane G-protein coupled receptor involved in taste transduction, which interacts with a G-protein to mediate taste signal transduction (see, e.g., Fong. *Cell Signal* 8:217(1996); Baldwin, *Curr. Opin. Cell Biol.* 6:180 (1994)). Structurally, exemplary polynucleotide sequences encoding rat, mouse, and human GPCR-B3 are presented in SEQ ID NOs:3-5, respectively, encoding polypeptides having the amino acid sequences of SEQ ID NOs:6-8. Exemplary polynucleotide sequences encoding rat, mouse, and human GPCR-B4 are presented in SEQ ID NOs:9-11, respectively, encoding polypeptides having the amino acid sequences of SEQ ID NOs:12-14. These taste receptors have been previously shown to be expressed in topographically distinct subpopulations of taste receptor cells and taste buds. These receptors are specifically localized to the taste pore, and are distantly related to putative mammalian pheromone receptors. The present invention thus demonstrates that Gα14 is specifically expressed in taste cells and further that it is co-expressed with GPCR-B3 and GPCR-B4 receptors in the different taste papillae. The G-protein alpha subunits that are specifically expressed in taste cells can thus be used, e.g., to screen for modulators of taste. The compounds identified by these assays would then be used by the food and pharmaceutical industries to customize taste, e.g., as additives to food or medicine so that the food or medicine tastes different to the subject who ingests it. For example, bitter medicines can be made to taste less bitter, and sweet substance can be enhanced.

In one aspect, the present invention provides a method for identifying a compound that modulates sensory signaling in sensory cells, the method comprising the steps of: (i) contacting the compound with a sensory cell specific G-protein alpha subunit polypeptide, the G-protein alpha subunit polypeptide comprising greater than about 70% amino acid sequence identity to a polypeptide having a sequence of SEQ ID NO:2; and (ii) determining a functional effect of the compound upon the G-protein alpha subunit polypeptide.

In one embodiment, the G-protein alpha subunit polypeptide specifically binds to polyclonal antibodies generated against SEQ ID NO:2. In another embodiment, the G-protein alpha subunit polypeptide is recombinant. In another embodiment, the G-protein alpha subunit polypeptide is from a mouse, a rat or a human. In another embodiment, the G-protein alpha subunit polypeptide comprises an amino acid sequence of SEQ ID NO:2. In another embodiment, the G-protein alpha subunit polypeptide is linked to a solid phase, either covalently or non-covalently. In another embodiment, the G-protein alpha subunit is a domain of a G-protein alpha subunit comprising greater than about 70% identity to a G-protein alpha subunit domain of a polypeptide having the amino acid sequence of SEQ ID NO:2. In another embodiment, the G-protein alpha subunit is a fusion polypeptide. In another embodiment, the G-protein alpha subunit is a domain fused to a heterologous polypeptide to form a fusion polypeptide.

In one embodiment, the functional effect is a chemical effect or a physical effect. In another embodiment, the functional effect is determined by measuring binding of radiolabeled GTP to the G-protein alpha subunit polypeptide or to a G protein comprising the G-protein alpha subunit polypeptide.

In one embodiment, the G-protein alpha subunit polypeptide is expressed in a cell or a cell membrane. In another embodiment, the cell or cell membrane is attached to a solid substrate. In another embodiment, the cell is a eukaryotic cell, e.g., a human cell, e.g., an HEK 293 cell. In another embodiment, the G-protein alpha subunit polypeptide is co-expressed with GPCR-B3 or GPCR-B4.

In one embodiment, the functional effect is determined by measuring changes in intracellular cAMP, cGMP, $IP_3$, DAG, or intracellular $Ca^{2+}$, e.g., using immunoassays. In another embodiment, the functional effect is measured by determining changes in the electrical activity of cells expressing the G-protein alpha subunit polypeptide, e.g., with an assay selected from the group consisting of a voltage clamp assay, a patch clamp assay, a radiolabeled ion flux assay, or a fluorescence assay using voltage sensitive dyes. In another embodiment, the functional effect is determined by measuring changes in the level of phosphorylation of sensory cell specific proteins. In another embodiment, the functional effect is determined by measuring changes in transcription levels of sensory cell specific genes.

In another aspect, the present invention provides a method for identifying a compound that modulates sensory signaling in sensory cells, the method comprising the steps of: (i) expressing a sensory cell specific G-protein alpha subunit polypeptide in an HEK 293 host cell, wherein the G-protein alpha subunit polypeptide comprises greater than about 70% amino acid sequence identity to a polypeptide having a sequence of SEQ ID NO:2; (ii) expressing a sensory cell specific G-protein coupled receptor in the host cell; (iii) contacting the host cell with the compound that modulates sensory signaling in sensory cells; and (iv) determining changes in intracellular calcium levels in the host cell.

BRIEF DESCRIPTION OF THE DRAWINGS

Not applicable.

DETAILED DESCRIPTION OF THE INVENTION

I. Introduction

The present invention demonstrates that nucleic acids encoding G-protein alpha 14 subunit are specifically expressed in taste cells. These nucleic acids and the polypeptides that they encode are referred to as "TC-Gα14" for "taste cell specific G-protein alpha 14 subunit." These taste cell specific nucleic acids and polypeptides are components of the taste transduction pathway and are G-protein alpha subunits involved in taste transduction.

The invention thus provides methods of screening for modulators, e.g., activators, inhibitors, stimulators, enhancers, agonists, and antagonists, of TC-Gα14. Such modulators of taste transduction are useful for pharmacological and genetic modulation of taste signaling pathways. These methods of screening can be used to identify high affinity agonists and antagonists of taste cell activity. These modulatory compounds can then be used in the food and pharmaceutical industries to customize taste. For example, the modulatory compounds would be added to a food or medicine, thereby altering its taste to the subject who ingests it.

Thus, the invention provides assays for taste modulation, where TC-Gα14 acts as a direct or indirect reporter molecule for the effect of modulators on taste transduction. TC-Gα14 can be used in assays, e.g., to measure changes in ion concentration, membrane potential, current flow, ion flux, transcription, signal transduction, receptor-ligand interactions, G-protein binding to receptors; binding to other G protein beta and gamma subunits; binding to enzymes; G-protein subunit ligand binding; second messenger concentrations, in vitro, in vivo, and ex vivo. In one embodiment, TC-Gα14 is recombinantly expressed in cells, optionally with taste specific GPCR such as GPCR-B3 or GPCR-B4, and modulation of taste transduction is assayed by measuring changes in $Ca^{2+}$ levels (see Example II). In another embodiment, binding of radiolabeled GTP to TC-Gα14 or a G-protein comprising TC-Gα14 is measured.

Methods of assaying for modulators of taste transduction include oocyte or tissue culture cell expression of TC-Gα14; transcriptional activation of TC-Gα14; phosphorylation and dephosphorylation of TC-Gα14; ligand binding assays; voltage, membrane potential and conductance changes; ion flux assays; changes in intracellular second messengers such as cAMP, cGMP, and inositol triphosphate; changes in intracellular calcium levels; and neurotransmitter release.

Finally, the invention provides for methods of detecting TC-Gα14 nucleic acid and protein expression, allowing investigation of taste transduction regulation and specific identification of taste receptor cells, as the nucleic acids are specifically expressed in taste cells. For example, probes for TC-Gα14 can be used to identify subsets of taste cells such as foliate cells and circumvallate cells, or specific taste receptor cells, e.g., sweet, sour, salty, and bitter. TC-Gα14 polypeptides can also be used to generate monoclonal and polyclonal antibodies useful for identifying taste receptor cells, e.g., in immuno histochemical assays. Taste receptor cells can be identified using techniques such as reverse transcription and amplification of mRNA, isolation of total RNA or poly $A^+$ RNA, northern blotting, dot blotting, in situ hybridization, RNase protection, S1 digestion, high density oligonucleotide arrays, western blots, and the like. The nucleic acids and the proteins that they encode also serve as tools for the generation of taste topographic maps that elucidate the relationship between the taste cells of the tongue and taste sensory neurons leading to taste centers in the brain. Furthermore, the nucleic acids and the proteins they encode can be used as probes to dissect taste-induced behaviors. TC-Gα14 also provides useful nucleic acid probes for paternity and forensic investigations.

Functionally, TC-Gα14 represents an alpha subunit of a heterotrimeric G-protein, which interacts with a GPCR to mediate taste signal transduction (see, e.g., Fong, *Cell Signal* 8:217 (1996); Baldwin, *Curr. Opin. Cell Biol.* 6:180 (1994)). G-proteins are composed of alpha, beta, and gamma subunits. The alpha subunit of a G-protein binds guanine nucleotide and is believed to confer receptor and effector specificity. G proteins mediate the interaction between G protein coupled receptors and signal transduction enzymes such as adenylate cyclase and phospholipase C.

Structurally, the nucleotide sequence of TC-Gα14 (see, e.g., SEQ ID NO:1 isolated from mouse) encodes a polypeptide of approximately 355 amino acids with a predicted molecular weight of approximately 41 kDa and a predicted range of 36-46 kDa (see, e.g., the amino acid sequence of Gα14 published in Wilkie et al., *PNAS USA* 88:10049-10053 (1991), SEQ ID NO:2). Related TC-Gα14 genes from other species share at least about 70% amino acid identity over an amino acid region at least about 25 amino acids in length, preferably 50 to 100 amino acids in length. TC-Gα14 is specifically expressed in taste receptor cells.

The present invention also provides polymorphic variants of the TC-Gα14 depicted in SEQ ID NO:2: variant #1, in which an isoleucine residue is substituted for the leucine residue at amino acid position 7; variant #2, in which an aspartic acid residue is substituted for the glutamic acid residue at amino acid position number 20; an variant #3, in which an alanine residue is substituted for the glycine residue at amino acid position 60.

Specific regions of the TC-Gα14 nucleotide and amino acid sequences may be used to identify polymorphic variants, interspecies homologs, and alleles of TC-Gα14. This identification can be made in vitro, e.g., under stringent hybridization conditions or with PCR and sequencing, or by using the sequence information in a computer system for comparison with other nucleotide or amino acid sequences. Typically, identification of polymorphic variants and alleles of TC-Gα14 is made by comparing an amino acid sequence of about 25 amino acids or more, preferably 50-100 amino acids. Amino acid identity of approximately at least about 70% or above, preferably 80%, most preferably 90-95% or above typically demonstrates that a protein is a polymorphic variant, interspecies homolog, or allele of TC-Gα14. Sequence comparison can be performed using any of the sequence comparison algorithms discussed below, preferably with the BLAST or BLAST 2.0 algorithm with default parameters, and either the BLASTN or BLASTP program with default parameters, as discussed below. Antibodies that bind specifically to TC-Gα14 or a conserved region thereof can also be used to identify alleles, interspecies homologs, and polymorphic variants.

Polymorphic variants, interspecies homologs, and alleles of TC-Gα14 are confirmed by examining taste cell specific expression of the putative TC-Gα14 polypeptide. Typically, TC-Gα14 having the amino acid sequence of SEQ ID NO:2 is used as a positive control, e.g., in immunoassays using antibodies directed against the amino acid sequence of SEQ ID NO:2, in comparison to the putative TC-Gα14 protein to demonstrate the identification of a polymorphic variant or allele of TC-Gα14. Alternatively, TC-Gα14 having the nucleic acid sequences of SEQ ID NO:1 is used as a positive control, e.g., in in situ hybridization with SEQ ID NO:1, in comparison to the putative TC-Gα14 nucleotide sequences to demonstrate the identification of a polymorphic variant or allele of TC-Gα14. The polymorphic variants, alleles and interspecies homologs of TC-Gα14 are expected to retain the ability to form a heterotrimeric G-protein.

TC-Gα14 nucleotide and amino acid sequence information may also be used to construct models of taste cell specific polypeptides in a computer system. These models are subsequently used to identify compounds that can activate or inhibit TC-Gα14. Such compounds that modulate the activity of TC-Gα4 can be used to investigate the role of TC-Gα14 in taste transduction or can be used as therapeutics.

Identification of taste cell specific expression of TC-Gα14 provides for the first time a means for assaying for inhibitors and activators of taste cell activity. TC-Gα14 is useful for testing taste modulators using in vivo and in vitro expression that measure, e.g., transcriptional activation of TC-Gα14; ligand binding; ligand binding (e.g., radiolabeled GTP binding to TC-Gα14 or a G-protein comprising TC-Gα14); phosphorylation and dephosphorylation; binding to G-proteins; G-protein activation; regulatory molecule binding; voltage, membrane potential and conductance changes; ion flux; intracellular second messengers such as cAMP, cGMP, and inositol triphosphate; intracellular calcium levels; and neurotransmitter release. Such activators and inhibitors identified using TC-Gα14 can be used to further study taste transduction and to identify specific taste agonists and antagonists. Such activators and inhibitors are useful as pharmaceutical and food agents for customizing taste.

Methods of detecting TC-Gα14 nucleic acids and expression of TC-Gα14 are also useful for identifying taste cells and creating topological maps of the tongue and the relation of tongue taste receptor cells to taste sensory neurons in the brain. Furthermore, these nucleic acids can be used to diagnose diseases related to taste by using assays such as northern blotting, dot blotting, in situ hybridization, RNase protection, and the like. Chromosome localization of the genes encoding human TC-Gα14 can be used to identify diseases, mutations, and traits caused by and associated with TC-Gα14. Techniques, such as high density oligonucleotide arrays (GeneChip™), can be used to screen for mutations, polymorphic variants, alleles and interspecies homologs of TC-Gα14.

II. Definitions

As used herein, the following terms have the meanings ascribed to them unless specified otherwise.

"Sensory cells" are cells that are found in sensory organs or parts thereof (e.g., taste buds, retina, olfactory epithelium, etc.) and that participate in sensing an external stimulus.

"Sensory cell specific" genes or proteins refer to those which are expressed exclusively, or preferentially, in the sensory cells but not in non-sensory cells.

"Taste cells" are neuroepithelial cells that are organized into groups to form taste buds of the tongue, e.g., foliate, fungiform, and circumvallate cells (see, e.g., Roper et al., Ann. Rev. Neurosci. 12:329-353 (1989)). Taste cells also include cells of the palate, and other tissues that may contain taste cells such as the esophagus and the stomach.

"Taste cell specific" genes or proteins refer to those which are expressed exclusively, or preferentially, in the taste cells but not in non-taste cells, or in subsets of Gustducin positive cells.

"Taste cell specific G-protein alpha subunit" or "TC-Gα14" refers to a G-protein alpha subunit that is specifically expressed in taste receptor cells such as foliate, fungiform, and circumvallate cells. Such taste cells can be identified because they express molecules such as Gustducin, a taste cell specific G-protein (McLaughin et al., Nature 357:563-569 (1992)). Taste receptor cells can also be identified on the basis of morphology (see, e.g., Roper, supra). TC-Gα encodes a G-protein alpha subunit with the ability to form a subunit of a heterotrimeric G-protein, that has "G-protein subunit activity," e.g., has the ability to form G-proteins that bind GTP. The alpha subunit binds guanine nucleotide and is believed to confer receptor and effector specificity. In response to extracellular stimuli, G-protein coupled receptors bind to G-proteins and promote production of second messengers such as $IP_3$, cAMP, and $Ca^{2+}$ via stimulation of enzymes such as phospholipase C and adenylate cyclase (for description of the structure and function of G-proteins and G-protein coupled receptors, see, e.g., Fong, supra, Baldwin, supra, McLaughlin, supra, Wilkie et al. PNAS USA 88:10049-10053 (1991)).

Protein "domains" such as a ligand binding domain, an active site, a subunit association region, etc. are found in the polypeptides of the invention. Such domains are useful for making chimeric proteins and for in vitro assays of the invention. These domains can be structurally identified using methods known to those of skill in the art, such as sequence analysis programs that identify hydrophobic and hydrophilic domains (see, e.g., Kyte & Doolittle, J. Mol. Biol. 157:105-132 (1982)).

A "TC-Gα14 domain" refers to a ligand binding domain, a subunit association domain, an active site, etc, identified as described above, that has at least about 70% identity to a a ligand binding domain, a subunit association domain, an active site, etc. from a polypeptide having a sequence of SEQ ID NO:2. Such domains can be used to make recombinant fusion proteins or chimeras, where a TC-Gα14 domain is fused to another molecule, such as a reporter molecule, e.g., Green Fluorescent Protein, β-gal, etc. Fusion proteins can also be made using a full length TC-Gα14 polypeptide.

The term "TC-Gα14" therefore refers to polymorphic variants, alleles, mutants, and interspecies homologs and TC-Gα14 domains thereof that: (1) have about 70% amino acid sequence identity, preferably about 75, 80, 85, 90 or 95% or higher amino acid sequence identity to SEQ ID NO:2 over a window of about 25 amino acids, preferably 50-100 amino acids; (2) bind to antibodies raised against an immunogen comprising an amino acid sequence of SEQ ID NO:2 and conservatively modified variants thereof; or (3) specifically hybridize (with a size of at least about 500, preferably at least about 900 nucleotides) under stringent hybridization conditions to a sequence SEQ ID NO:1, and conservatively modified variants thereof. This term also refers to a domain of TC-Gα14 as described above.

"TC-GPCR" refers to a G-protein coupled receptor that is specifically expressed in taste receptor cells such as foliate, fungiform, and circumvallate cells. Such taste cells can be identified because they express molecules such as Gustducin, a taste cell specific G-protein (McLaughlin et al., Nature 357:563-569 (1992)). Taste receptor cells can also be identified on the basis of morphology (see, e.g., Roper, supra). Examples of TC-GPCR include GPCR-B3 and GPCR-B4 (see, e.g., Hoon et al., Cell 96:541-551 (1999); see also U.S. Ser. No. 09/361,652, filed Jul. 27, 1999 and U.S. Ser. No. 09/361,631, filed Jul. 27, 1999), now U.S. Pat. No. 6,383, 778), herein incorporated by reference in their entirety). Exemplary polynucleotide sequences encoding rat, mouse, and human GPCR-B3 are presented in SEQ ID NOs:3-5, respectively, encoding polypeptides having the amino acid sequences of SEQ ID NOs:6-8. Exemplary polynucleotide sequences encoding rat, mouse, and human GPCR-B4 are presented in SEQ ID NOs:9-11, respectively, encoding polypeptides having the amino acid sequences of SEQ ID NOs:12-14. TC-GPCRs encode G-protein coupled receptors with seven transmembrane regions that have "G-protein coupled receptor activity," as described below, e.g., they bind to G-proteins in response to extracellular stimuli and promote production of second messengers such as $IP_3$, cAMP, and $Ca^{2+}$ via stimulation of enzymes such as phospholipase C and adenylate cyclase (for a description of the structure and function of G-protein coupled receptors, see, e.g., Fong, supra, and Baldwin, supra).

"GPCR activity" refers to the ability of a GPCR to transduce a signal. Such activity can be measured in a heterologous cell, by coupling a GPCR (or a chimeric GPCR) to either an endogenous G-protein, a promiscuous G-protein subunit such as Gα15, or a taste specific G-protein subunit such as TC-Gα14, and an enzyme such as PLC, and measuring increases in intracellular calcium using (Offermans & Simon, J. Biol. Chem. 270:15175-15180 (1995)). Receptor activity can be effectively measured by recording ligand-induced changes in $[Ca^{2+}]_i$ using fluorescent $Ca^{2+}$-indicator dyes and fluorometric imaging. Optionally, the polypeptides of the invention are involved in sensory transduction, optionally taste transduction in taste cells.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, HEK 293 and the like.

"Biological sample" as used herein is a sample of biological tissue or fluid that contains nucleic acids or polypeptides of TC-Gα14. Such samples include, but are not limited to, tissue isolated from humans, mice, and rats, in particular, tongue. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans. Preferred tissues include tongue tissue and isolated taste buds.

The phrase "functional effects" in the context of assays for testing compounds that modulate TC-Gα14 mediated taste transduction includes the determination of any parameter that is indirectly or directly under the influence of TC-Gα14 or a G-protein comprising TC-Gα14, e.g., a functional, physical, or chemical effect. It includes ligand binding, changes in ion flux, membrane potential, current flow, radiolabled GTP binding, subunit association, transcription, G-protein binding, GPCR phosphorylation or dephosphorylation, signal transduction, receptor-ligand interactions, second messenger concentrations (e.g., cAMP, cGMP, $IP_3$, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of TC-Gα14, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, radiolabeled GTP binding, oocyte TC-Gα14 expression; tissue culture cell TC-Gα14 expression; transcriptional activation of TC-Gα14; ligand binding assays; voltage, membrane potential and conductance changes; ion flux assays; changes in intracellular second messengers such as cAMP and inositol triphosphate (IP3); changes in intracellular calcium levels; neurotransmitter release, and the like.

"Inhibitors," "activators," and "modulators" of TC-Gα14 are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize or up regulate taste transduction, e.g., agonists. Modulators include compounds that, e.g., alter the interaction of a polypeptide with: G protein coupled receptors; extracellular proteins that bind activators or inhibitor (e.g., ebnerin and other members of the hydrophobic carrier family); G-proteins; G protein alpha and beta subunits ; kinases (e.g., homologs of rhodopsin kinase and beta adrenergic receptor kinases that are involved in deactivation and desensitization of a receptor); and arrestin-like proteins, which also deactivate and desensitize receptors. Modulators include genetically modified versions of TC-Gα14, e.g., with altered activity, as well as naturally occurring and synthetic ligands, antagonists, agonists, small chemical molecules and the like. Such assays for inhibitors and activators include, e.g., expressing TC-Gα14 in vitro, in cells, or cell membranes, applying putative modulator compounds, and then determining the functional effects on taste transduction, as described above.

Samples or assays comprising TC-Gα14 that are treated with a potential activator, inhibitor, or modulator are compared to control samples without the inhibitor, activator, or modulator to examine the extent of inhibition. Control samples (untreated with inhibitors) are assigned a relative TC-Gα14 activity value of 100%. Inhibition of TC-Gα14 is achieved when the TC-Gα14 activity value relative to the control is about 80%, preferably 50%, more preferably 25-0%. Activation of TC-Gα14 is achieved when the TC-Gα14 activity value relative to the control (untreated with activators) is 110%, more preferably 150%, more preferably 200-500% (i.e., two to five fold higher relative to the control), more preferably 1000-3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated TC-Gα4 nucleic acid is separated from open reading frames that flank the TC-Gα14 gene and encode proteins other than TC-Gα14. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Biologically active" TC-Gα14 refers to TC-Gα14 having taste transduction activity in taste receptor cells or in an assay system with additional signal transduction components of the taste transduction system.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al.,

*Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which ant or 7 can be made detectable, e.g., by incorporating a radiolabel into the peptide, and used to detect antibodies specifically reactive with the peptide).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region (see, e.g., SEQ ID NO:2)), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, ascoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to V$_H$-C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-TC-Gα14" antibody is an antibody or antibody fragment that specifically binds a polypeptide encoded by the TC-Gα14 gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to TC-Gα14 from specific species such as rat, mouse, or human can be selected to obtain only those polyclonal antibodies that are specifically immunoreactive with TC-Gα14, and not with other proteins, except for polymorphic variants and alleles of TC-Gα14. This selection may be achieved by subtracting out antibodies that cross-react with TC-Gα14 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

III. Assays for Taste Modulation

A. Assays for Taste Cell Specific G-Protein Alpha Subunit Activity

TC-Gα14 and its alleles, interspecies homologs, and polymorphic variants participate in taste transduction. The activity of TC-Gα14 polypeptides, domains thereof, or fusion proteins of a TC-Gα14 polypeptide or a domain thereof can be assessed using a variety of in vitro and in vivo assays that measure functional, chemical and physical effects, e.g., measuring ligand binding (e.g., radioactive ligand or GTP binding), signal transduction enzyme activity (e.g., adenylate cyclase or phospholipase C), second messengers (e.g., cAMP, cGMP, IP$_3$, DAG, or Ca$^{2+}$), ion flux, phosphorylation levels, transcription levels, neurotransmitter levels, and the like. Furthermore, such assays can be used to screen for activators, inhibitors, and modulators of TC-Gα14. Such activators, inhibitors, and modulators of taste transduction activity are useful for customizing taste.

The TC-Gα14 of the assay will be selected from a polypeptide having a sequence of SEQ ID NO:2 or alleles, orthologs, polymorphic variants, and conservatively modified variant thereof, e.g., from humans, rats, or mice. Alternatively, the TC-Gα14 of the assay will be derived from a eukaryote and include an amino acid subsequence having at least about 70% amino acid sequence identity SEQ ID NO:2. Generally, the amino acid sequence identity will be at least 70%, optionally at least 75%, 80%, 85%, optionally at least 90-95%. Optionally, the polypeptide of the assays will comprise a domain of TC-Gα14, such as a ligand binding domain, subunit association domain, active site, and the like. Either TC-Gα14 or a domain thereof can be covalently linked to a heterologous protein to create a chimeric protein used in the assays described herein.

Modulators of TC-Gα14 activity are tested using TC-Gα14 polypeptides, chimeras or fragments thereof, as described above, either recombinant or naturally occurring. The protein can be isolated, expressed in a cell, expressed in a membrane derived from a cell, expressed in tissue or in an animal, in any case either recombinant or naturally occurring. For example, tongue slices, dissociated cells from a tongue, transformed cells, cell membranes, or lipid bilayers can be used. Modulation is tested using one of the in vitro or in vivo assays described herein. Taste transduction can also be examined in vitro with soluble or solid state reactions, using a chimeric molecule, comprising, e.g., a ligand binding domain of TC-Gα14, or a domain of TC-Gα14, or a full-length TC-Gα14. Furthermore, ligand-binding domains of the protein of interest can be used in vitro in soluble or solid state reactions to assay for ligand binding.

The effects of the test compounds upon the function of the polypeptides can be measured by examining any of the parameters described herein. Any suitable physiological change that affects TC-Gα14 activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Samples or assays that are treated with a test compound which potentially activates, inhibits, or modulates TC-Gα14 are compared to control samples that are not treated without the test compound, to examine the extent of modulation. Control samples (untreated with activators, inhibitors, or modulators) are assigned a relative TC-Gα14 activity value of 100%. Inhibition of TC-Gα14 is achieved when the TC-Gα14 activity value relative to the control is about 90% (e.g., 10% less than the control), preferably 50%, more preferably 25-0%. Activation of TC-Gα4 is achieved when the TC-Gα14 activity value relative to the control is 110% (e.g., 10% more than the control), more preferably 150%, more preferably 200-500%, more preferably 1000-2000%.

In one embodiment, ligand binding to TC-Gα14, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties. In one example, radiolabeled GTP is used.

In another embodiment, receptor-G protein interactions are examined. For example, binding of a G protein comprising TC-Gα14 to a receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors. An activator can be added to the receptor and G protein in the absence of GTP, forming a tight complex, and then screen for inhibitors can be performed by looking at dissociation of the receptor-G protein complex. In the presence of GTP, release of the alpha subunit of the G protein from the other two G protein subunits serves as a criterion of activation.

In another example, activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G proteins. The kinase/arrestin pathway plays a key role in the desensitization of many GPCR receptors. For example, compounds that modulate the duration a taste receptor stays active would be useful as a means of prolonging a desired taste or cutting off an unpleasant one. For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., *Nature* 348:125-32 (1990); Pitcher et al., *Annu. Rev. Biochem.* 67:653-92 (1998).

In another embodiment, signal transduction enzymes and second messengers are examined. An activated or inhibited G protein will in turn alter the properties of target enzymes, channels, and other effector proteins. The classic examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Signal transduction typically initiates subsequent intracellular events via, e.g., G-proteins and/or other enzymes, such as adenylate cyclase or phospholipase C, which are downstream from the G-proteins in taste transduction pathways. For example, receptor activation and signal transduction may result in a change in the level of intracellular cyclic nucleotides, e.g., cAMP or cGMP, by activating or inhibiting enzymes such as adenylate cyclase by G-protein α and βγ subunits. These intracellular cyclic nucleotides, in turn, may modulate other molecules, such as cyclic nucleotide-gated ion channels, e.g., channels that are made permeable to cations by binding of cAMP or cGMP such as e.g., rod photoreceptor cell channels and olfactory neuron channels (see, e.g., Altenhofen et al., *Proc. Natl. Acad. Sci. U.S.A.* 88:9868-9872 (1991) and Dhallan et al., *Nature* 347:184-187 (1990)). In cases where activation of TC-Gα4 results in a decrease in cyclic nucleotide levels, it may be preferable to expose the cells to agents that increase intracellular cyclic nucleotide levels, e.g., forskolin, prior to adding a modulatory compound to the cells in the assay. Cells for this type of assay can be made by co-transfection of a host cell with DNA encoding a cyclic nucleotide-gated ion channel, DNA encoding TC-Gα14, DNA encoding a GPCR phosphatase and DNA encoding a G-protein coupled receptor (e.g., metabotropic glutamate receptors, muscarinic acetylcholine receptors, dopamine receptors, serotonin receptors, and the like), which, when activated, causes a change in cyclic nucleotide levels in the cytoplasm.

In response to external stimuli, certain G-protein coupled receptors may activate an effector such as phospholipase C, through G-proteins. Activation of phospholipase C results in the production of inositol 1,4,5-triphosphate ($IP_3$) and diacylglycerol (DAG) from inositol 4,5-biphosphate ($PIP_2$) (Berridge & Irvine, *Nature* 312:315-21 (1984)). $IP_3$ in turn stimulates the release of intracellular calcium ion stores. Cells may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Thus, a change in the level of second messengers, such as $IP_3$, DAG, or $Ca^{2+}$ can be used to assess TC-Gα14 function. Furthermore, a change in the level of these second messengers can be used to screen for activators, inhibitors, and modulators of TC-Gα14 polypeptides.

For example, the activity of TC-Gα14 polypeptides can be assessed by measuring, e.g., changes in intracellular second messengers, such as cAMP, cGMP, $IP_3$, DAG, or $Ca^{2+}$. Therefore, the second messenger levels can be used as reporters for potential activators, inhibitors, and modulators of TC-Gα14 polypeptides. In one embodiment, the changes in intracellular cAMP or cGMP can be measured using immunoassays. The method described in Offermanns & Simon, *J. Biol. Chem.* 270:15175-15180 (1995) may be used to determine the level of cAMP. Also, the method described in Felley-Bosco et al., *Am. J. Resp. Cell and Mol. Biol.* 11:159-164 (1994) may be used to determine the level of cGMP. Further, an assay kit for measuring cAMP and/or cGMP is described in U.S. Pat. No. 4,115,538, herein incorporated by reference.

In another example, the second messenger phosphatidyl inositol (PI) hydrolysis can be analyzed according to U.S. Pat. No. 5,436,128, herein incorporated by reference. Briefly, the assay involves labeling of cells with $^3$H-myo-inositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another example, intracellular $Ca^{2+}$ levels can be analyzed, e.g., using fluorescent $Ca^{2+}$ indicator dyes and fluorometric imaging (see, e.g., Hall et al., *Nature* 331:729 (1988); Kudo et al., *Neuros.* 50:619-625 (1992); van Heugten et al., *J. Mol. Cell. Cardiol.* 26:1081-93 (1994)).

In another embodiment, the activity of TC-Gα14 can also be assessed by measuring changes in ion flux. Changes in ion flux may be measured by determining changes in polarization (i.e., electrical potential) of the cell or membrane expressing TC-Gα14. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575-1595 (1997)). Whole cell currents are conveniently determined using the standard methodology (see, e.g., Hamil et al., *PFlugers. Archiv.* 391:85 (1981)). Other known assays include: radiolabeled ion flux assays and fluorescence assays using voltage-sensitive dyes (see, e.g., Vestergarrd-Bogind et al., *J. Membrane Biol.* 88:67-75 (1988); Gonzales & Tsien, *Chem. Biol.* 4:269-277 (1997); Daniel et al., *J. Pharmacol. Meth.* 25:185-193 (1991); Holevinsky et al., *J. Membrane Biology* 137:59-70 (1994)). A method for the whole-cell recording from non-dissociated taste cells within mouse taste bud is described in Miyamoto et al., *J. Neurosci Methods* 64:245-252 (1996). Therefore, changes in ion flux can be used to screen for activators, inhibitors, and modulators of TC-Gα14. Generally, the compounds to be tested are present in the range from 1 pM to 100 mM.

Assays for measuring changes in ion flux include cells that are loaded with ion or voltage sensitive dyes to report TC-Gα14 activity. Assays for determining activity of these polypeptides can also use known agonists and antagonists for these polypeptides as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog.

In another embodiment, phosphorylation of taste cell specific proteins can be measured to assess the effects of a test compound on TC-Gα14 function. This can be achieved by using a method disclosed in, e.g., U.S. Pat. No. 5,834,216, herein incorporated by reference. A duplicate cell culture containing expressed TC-Gα14 can be prepared. One of the duplicate cultures is exposed to a test compound. Cell lysates from the duplicate cultures are prepared. The cell lysates are contacted with ATP or a GTP, wherein the nucleotide has a gamma-phosphate having a detectable label, or an analog of a gamma phosphate (i.e., having a label capable of being transferred to a phosphorylation site such as gamma $S^{35}$). The level of phosphorylated taste cell specific proteins may be measured by precipitating the cell lysates with an antibody specific for taste cell specific proteins. After precipitation, phosphorylated (labeled) taste cell specific proteins may be separated from other cellular proteins by electrophoresis or by chromatographic methods. By way of example, labeled taste cell specific proteins may be separated on denaturing polyacrylamide gels after which the separated proteins may be transferred to, for example, a nylon or nitrocellulose membrane followed by exposure to X-ray film. Relative levels of phosphorylation are then determined after developing the exposed X-ray film and quantifying the density of bands corresponding to the taste cell specific proteins, for example, densitometry. The autoradiograph may also be used to localize the bands on the membrane corresponding to labeled taste cell specific proteins after which they may be excised from the membrane and counted by liquid scintillation or other counting methods. Using this method, a test compound which effects the function of TC-Gα14 is identified by its ability to increase or decrease phosphorylation of taste cell specific proteins compared to control cells not exposed to the test compound.

In another embodiment, transcription levels can be measured to assess the effects of a test compound on TC-Gα14 function. A host cell containing TC-Gα14 is contacted with a test compound for a sufficient time to effect any interactions, and then the level of TC-Gα14 gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of TC-Gα14 may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, TC-Gα14 can be used as indirect reporters via attachment to a second reporter such as green fluorescent protein (see, e.g., Mistili & Spector, *Nature Biotechnology* 15:961-964 (1997)).

The amount of transcription is then compared to the amount of transcription in either the same cell in the absence of the test compound, or it may be compared with the amount of transcription in a substantially identical cell that lacks TC-Gα14. A substantially identical cell may be derived from the same cells from which the recombinant cell was prepared but which had not been modified by introduction of heterologous DNA. Any difference in the amount of transcription indicates that the test compound has in some manner altered the activity of TC-Gα14.

Other physiological change that affects TC-Gα14 activity can be used to assess the influence of a test compound on the polypeptides of this invention. For example, the influence of a test compound on the GTPase activity of TC-Gα14 can be assessed using the method described in U.S. Pat. No. 5,817,759, which patent is incorporated herein by reference. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and the like.

In a preferred embodiment, TC-Gα14 activity is measured by expressing TC-Gα14 in a heterologous cell with a TC-GPCR (see U.S. Ser. No. 09/361,652, filed Jul. 27, 1999 and U.S. Ser. No. 09/361,631, filed Jul. 27, 1999), now U.S. Pat. No. 6,383,778). Exemplary polynucleotide sequences encoding rat, mouse, and human GPCR-B3 are presented in SEQ ID NOs:3-5, respectively, encoding polypeptides having the amino acid sequences of SEQ ID NOs:6-8. Exemplary polynucleotide sequences encoding rat, mouse, and human GPCR-B4 are presented in SEQ ID NOs:9-11, respectively, encoding polypeptides having the amino acid sequences of SEQ ID NOs:12-14. As shown in Example I below, TC-Gα14 is specifically expressed in taste receptor cells, and also co-expressed with GPCR-B3 and GPCR-B4, in different taste papillae. As described above, HEK-293 cells may be used as a heterologous host cell, and modulation of taste transduction is assayed by measuring changes in intracellular $Ca^{2+}$ levels.

B. Modulators

The compounds tested as modulators of TC-Gα14 can be any small chemical compound, or a biological entity, such as a protein, sugar, nucleic acid or lipid. Alternatively, modulators can be genetically altered versions of TC-Gα14. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. *J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing TC-Gα14 is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000-20,000 different compounds is possible using the integrated systems of the invention. More recently, microfluidic approaches to reagent manipulation have been developed.

C. Solid State and Soluble High throughput Assays

In one embodiment the invention provide soluble assays using molecules such as a domain such as ligand binding domain, an active site, a subunit association region, etc.; a domain that is covalently linked to a heterologous protein to create a chimeric molecule; TC-Gα14; a cell or tissue expressing TC-Gα14, either naturally occurring or recombinant. In another embodiment, the invention provides solid phase based in vitro assays in a high throughput format, where the domain, chimeric molecule, TC-Gα14, or cell or tissue expressing TC-Gα14 is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000-20,000 different compounds is possible using the integrated systems of the invention.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalized a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-Based assays

Yet another assay for compounds that modulate TC-Gα14 activity involves computer assisted drug design, in which a computer system is used to generate a three-dimensional structure of TC-Gα14 based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering G-protein amino acid sequences of at least 10 amino acid residues or corresponding nucleic acid sequences encoding a TC-Gα14 polypeptide into the computer system. The amino acid sequence of the polypeptide of the nucleic acid encoding the polypeptide is selected from the group consisting of SEQ ID NO:2 and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art. The three-dimensional structural model of the protein can be saved to a computer readable form and be used for further analysis (e.g., identifying potential ligand binding regions of the protein and screening for mutations, alleles and interspecies homologs of the gene).

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the TC-Gα4 protein to identify ligands that bind to TC-Gα14. Binding affinity between the protein and ligands is determined using energy terms to determine which ligands have an enhanced probability of binding to the protein. The results, such as three-dimensional structures for potential ligands and binding affinity of ligands, can also be saved to a computer readable form and can be used for further analysis (e.g., generating a three dimensional model of mutated proteins having an altered binding affinity for a ligand).

Computer systems are also used to screen for mutations, polymorphic variants, alleles and interspecies homologs of TC-Gα14 genes. Such mutations can be associated with disease states or genetic traits. As described above, high density oligonucleotide arrays (GeneChip™) and related technology can also be used to screen for mutations, polymorphic variants, alleles and interspecies homologs. Once the variants are identified, diagnostic assays can be used to identify patients having such mutated genes. Identification of the mutated TC-Gα14 genes involves receiving input of a first nucleic acid or amino acid sequence encoding TC-Gα14, selected from the group consisting of SEQ ID NO:1, or SEQ ID NO:2, and conservatively modified versions thereof. The sequence is entered into the computer system as described above and then saved to a computer readable form. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in TC-Gα14 genes, and mutations associated with disease states and genetic traits.

III. Isolation of the Nucleic Acid Encoding TC-Gα14

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding TC-Gα14

In general, the nucleic acid sequences encoding TC-Gα14 and related nucleic acid sequence homologs are cloned from cDNA and genomic DNA libraries by hybridization with a probe, or isolated using amplification techniques with oligonucleotide primers. For example, TC-Gα14 sequences are typically isolated from mammalian nucleic acid (genomic or cDNA) libraries by hybridizing with a nucleic acid probe, the sequence of which can be derived from SEQ ID NO:1. The mouse sequence of SEQ ID NO:1 can be used to isolate orthologs from other species, such as human and rat. A suitable tissue from which TC-Gα14 RNA and cDNA can be isolated is tongue tissue, preferably taste bud tissue, more preferably individual taste cells. For example, circumvallate, foliate, fungiform taste receptor cells can be used to isolate TC-Gα14 RNA and cDNA.

Amplification techniques using primers can also be used to amplify and isolate TC-Gα14 from DNA or RNA (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for full-length TC-Gα14.

Nucleic acids encoding TC-Gα14 can also be isolated from expression libraries using antibodies as probes. Such polyclonal or monoclonal antibodies can be raised using the sequence of SEQ ID NO:2.

Polymorphic variants, alleles, and interspecies homologs that are substantially identical to TC-Gα14 can be isolated using TC-Gα14 nucleic acid probes, and oligonucleotides under stringent hybridization conditions, by screening libraries. Alternatively, expression libraries can be used to clone TC-Gα14, and its polymorphic variants, alleles, and interspecies homologs, by detecting expressed homologs immunologically with antisera or purified antibodies made against TC-Gα14, which also recognize and selectively bind to the TC-Gα14 homolog.

To make a cDNA library, one should choose a source that is rich in TC-Gα14 mRNA, e.g., tongue tissue, or isolated taste buds. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating TC-Gα14 nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of TC-Gα14 directly from mRNA, from cDNA, from genomic libraries or cDNA libraries. Degenerate oligonucleotides can be designed to amplify TC-Gα14 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of TC-Gα14 encoding mRNA in physiological samples, for nucleic acid sequencing, or for other purposes. Genes amplified by the PCR reaction can be purified from agarose gels and cloned into an appropriate vector.

Gene expression of TC-Gα14 can also be analyzed by techniques known in the art, e.g., reverse transcription and amplification of mRNA, isolation of total RNA or poly A⁺ RNA, northern blotting, dot blotting, in situ hybridization, RNase protection, and the like. In one embodiment, high density oligonucleotide arrays technology (e.g., Gene-Chip™) is used to identify homologs and polymorphic variants of the TC-Gα14 of the invention (see, e.g., Gunthand et al., *AIDS Res. Hum. Retroviruses* 14:869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998)).

Synthetic oligonucleotides can be used to construct recombinant TC-Gα14 genes for use as probes or for expression of protein. This method is performed using a series of overlapping oligonucleotides usually 40-120 bp in length, representing both the sense and non-sense strands of the gene. These DNA fragments are then annealed, ligated and cloned. Alternatively, amplification techniques can be used with precise primers to amplify a specific subsequence of the TC-Gα14 nucleic acid. The specific subsequence is then ligated into an expression vector.

Optionally, nucleic acids encoding chimeric proteins comprising TC-Gα14 or domains thereof can be made according to standard techniques. For example, a domain such as ligand binding domain, an active site, a subunit association region, a membrane binding domain etc., can be covalently linked to a heterologous protein. Heterologous proteins of choice include, e.g., green fluorescent protein, β-gal, glutamate receptor, and the rhodopsin presequence.

The nucleic acid encoding TC-Gα14 is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene or nucleic acid, such as those cDNAs encoding TC-Gα14, one typically subclones TC-Gα14 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the TC-Gα14 proteins are available in, e.g., *E. coli, Bacillus sp.*, and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the TC-Gα14 encoding nucleic acid in host cells. A typical expression cassette thus contains a promoter operably linked to the nucleic acid sequence encoding TC-Gα14 and signals required for efficient polyadenylation of the transcript, ribosome binding sites, and translation termination. The nucleic acid sequence encoding TC-Gα14 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a TC-Gα14 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of TC-Gα14 proteins, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983)).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing TC-Gα14.

After the expression vector is introduced into the cells, the transfected cells are cultured under conditions favoring expression of TC-Gα14, which is recovered from the culture using standard techniques identified below.

IV. Purification of TC-Gα14

Either naturally occurring or recombinant TC-Gα14 can be purified for use in functional assays. Preferably, recombinant TC-Gα14 is purified. Naturally occurring TC-Gα14 is purified, e.g., from mammalian tissue such as tongue tissue, and any other source of a TC-Gα14 homolog. Recombinant TC-Gα14 is purified from any suitable expression system.

TC-Gα14 may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant TC-Gα14 is being purified. For example, proteins having established molecular adhesion properties can be reversible fused to TC-Gα14. With the appropriate ligand, TC-Gα14 can be selectively adsorbed to a purification column and then freed from the column in a relatively pure form. The fused protein is then removed by enzymatic activity. Finally TC-Gα14 could be purified using immunoaffinity columns.

A. Purification of TC-Gα14 from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of TC-Gα14 inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-formin G-proteins, for example SDS (sodium dodecyl sulfate), 70% formic acid, are inappropriate for use in this procedure due to the possibility of irreversible denaturation of the proteins, accompanied by a lack of immunogenicity and/or activity.

Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. TC-Gα14 is separated from other bacterial proteins by standard separation techniques, e.g., with Ni-NTA agarose resin.

Alternatively, it is possible to purify TC-Gα14 from bacteria periplasm. After lysis of the bacteria, when TC-Gα14 is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying TC-Gα14

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of TC-Gα14 can be used to isolate them from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

TC-Gα14 can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of TC-Gα14

In addition to the detection of TC-Gα14 genes and gene expression using nucleic acid hybridization technology, one can also use immunoassays to detect TC-Gα14, e.g., to identify taste receptor cells and variants of TC-Gα14. Immunoassays can be used to qualitatively or quantitatively analyze TC-Gα14. A general overview of the applicable technology can be found in Harlow & Lane, *Antibodies: A Laboratory Manual* (1988).

A. Antibodies to TC-Gα14

Methods of producing polyclonal and monoclonal antibodies that react specifically with TC-Gα14 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of TC-Gα14 comprising immunogens may be used to produce antibodies specifically reactive with TC-Gα14. For example, recombinant TC-Gα14 or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring G-protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to TC-Gα14. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511-519 (1976)).

Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non TC-Gα14 proteins or even other related proteins from other organisms, using a competitive binding immunoassay. Specific polyclonal antisera and monoclonal antibodies will usually bind with a $K_d$ of at least about 0.1 mM, more usually at least about 1 μM, preferably at least about 0.1 μM or better, and most preferably, 0.01 μM or better.

Once TC-Gα14 specific antibodies are available, TC-Gα14 can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

TC-Gα14 can be detected and/or quantified using any of a number of well recognized immunological binding assays (see, e.g., U.S. Pat. Nos. 4,366,241; 4,376,110; 4,517,288; and 4,837,168). For a review of the general immunoassays, see also, *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the TC-Gα14, or antigenic subsequence thereof). The antibody (e.g., anti-TC-Gα14) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled polypeptide of TC-Gα14 or a labeled anti-TC-Gα14 antibody. Alternatively, the labeling agent may be a third moiety, such a secondary antibody, that specifically binds to the antibody/TC-Gα14 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-comipetitive Assay Formats

Immunoassays for detecting TC-Gα14 in samples may be either competitive or noncompetitive. Noncompetitive immunoassays are assays in which the amount of antigen is directly measured. In one preferred "sandwich" assay, for example, the anti-TC-Gα14 antibodies can be bound directly to a solid substrate on which they are immobilized. These immobilized antibodies then capture TC-Gα14 present in the test sample. TC-Gα14 is thus immobilized is then bound by a labeling agent, such as a second TC-Gα14 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of TC-Gα14 present in the sample is measured indirectly by measuring the amount of a known, added (exogenous) TC-Gα14 displaced (competed away) from an anti-TC-Gα14 antibody by the unknown TC-Gα14 present in a sample. In one competitive assay, a known amount of TC-Gα14 is added to a sample and the sample is then contacted with an antibody that specifically binds to TC-Gα14. The amount of exogenous TC-Gα14 bound to the antibody is inversely proportional to the concentration of TC-Gα14 present in the.sample. In a particularly preferred embodiment, the antibody is immobilized on a solid substrate. The amount of TC-Gα14 bound to the antibody may be determined either by measuring the amount of TC-Gα14 present in a TC-Gα14/antibody complex, or alternatively by measuring the amount of remaining uncomplexed protein. The amount of TC-Gα14 may be detected by providing a labeled TC-Gα14 molecule.

A hapten inhibition assay is another preferred competitive assay. In this assay the known TC-Gα14, is immobilized on a solid substrate. A known amount of anti-TC-Gα14 antibody is added to the sample, and the sample is then contacted with the immobilized TC-Gα14. The amount of anti-TC-Gα14 antibody bound to the known immobilized TC-Gα14 is inversely proportional to the amount of TC-Gα14 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein at least partially encoded by SEQ ID NO:2 can be immobilized to a solid support. Proteins (e.g., TC-Gα14 proteins and homologs) are added to the assay that compete for binding of the antisera to the immobilized antigen. The ability of the added proteins to compete for binding of the antisera to the immobilized protein is compared to the ability of TC-Gα14 encoded by SEQ ID NO:2 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of TC-Gα14 to the immunogen protein (i.e., TC-Gα14 of SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a TC-Gα14 immunogen.

Other Assay Formats

Western blot (immunoblot) analysis is used to detect and quantify the presence of TC-Gα14 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind TC-Gα14. The anti-TC-Gα14 antibodies specifically bind to TC-Gα14 on the solid support. These antibodies may be directly labeled or alternatively may be subsequently detected using labeled antibodies (e.g., labeled sheep anti-mouse antibodies) that specifically bind to the anti-TC-Gα14 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize TC-Gα14, or secondary antibodies that recognize anti-TC-Gα14.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VIII. Kits

TC-Gα14 and its homologs are a useful tool for identifying taste receptor cells, for forensics and paternity determinations, and for examining taste transduction (e.g., generating a topographical map between the taste cells of the tongue and the corresponding taste centers in the brain). Specific reagents that specifically hybridize to TC-Gα14 nucleic acid, such as its probes and primers, and specific reagents that specifically bind to the TC-Gα14 protein, e.g., its antibodies are used to examine taste cell expression and taste transduction regulation.

Nucleic acid assays for the presence of TC-Gα14 DNA and RNA in a sample include numerous techniques are known to those skilled in the art, such as Southern analysis, northern analysis, dot blots, RNase protection, high density oligonucleotide arrays, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230-250 (1986); Haase et al., *Methods in Virology*, vol. VII, pp. 189-226 (1984); and *Nucleic Acid Hybridization: A Practical Approach* (Hames et al., eds. 1987). In addition, TC-Gα14 protein can be detected with the various immunoassay techniques described above. The test sample is typically compared to both a positive control (e.g., a sample expressing recombinant TC-Gα14) and a negative control.

The present invention also provides for kits for screening for modulators of TC-Gα14. Such kits can be prepared from readily available materials and reagents. For example, such kits can comprise any one or more of the following materials: TC-Gα14, reaction tubes, and instructions for testing TC-Gα14 activity. Preferably, the kit contains biologically active TC-Gα14. A wide variety of kits and components can be prepared according to the present invention, depending upon the intended user of the kit and the particular needs of the user.

IX. Administration and Pharmaceutical Compositions

Taste modulators can be administered directly to the mammalian subject for modulation of taste in vivo. Administration is by any of the routes normally used for introducing a modulator compound into ultimate contact with the tissue to be treated, preferably the tongue or mouth. The taste modulators are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, $17^{th}$ ed. 1985)).

The taste modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoneally, intravesically or intrathecally. Preferably, the compositions are administered orally or nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular taste modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered in a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, taste modulators of the present invention can be administered at a rate determined by the LD-50 of the modulator, and the side-effects of the inhibitor at various concentrations, as applied to the mass and overall health of the subject. Administration can be accomplished via single or divided doses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Taste Receptor Cell Specific Expression of TC-Gα14

Clones representing different Gα subunits were amplified by PCR and labeled for in situ hybridizations with tongue sections. These include $G\alpha_s$, $G\alpha_{i1}$, $G\alpha_{i2}$, $G\alpha_{i3}$, $G\alpha_z$, $G\alpha_{t1}$, $G\alpha_{t2}$, $G\alpha_{olf}$, $G\alpha_q$, $G\alpha_{11}$, $G\alpha_{12}$, $G\alpha_{14}$ and $G\alpha_{15}$ (see Simon et al., *Science* 252:802-8 (1991)). $G\alpha_{14}$ amino acid sequence is published in Wilkie et al. *PNAS USA* 88:10049-10053 (1991). Taste tissue was obtained from adult rats and mice. No sex-specific differences in expression patterns were observed, therefore male and female animals were used interchangeably. For foliate sections, no differences in expression pattern were observed between the papillae. Fresh frozen sections (14 μm) were attached to silanized slides and prepared for in situ hybridization as described previously (Ryba & Tirindelli, *Neuron* 19:371-379 (1997)). All in situ hybridizations were carried out at high stringency (5×SSC, 50% formamide, 72° C.). For single-label detection, signals were developed using alkaline-phosphatase conjugated antibodies to digoxigenin and standard chromogenic substrates (Boehringer Mannheim). For double-label fluorescent detection, an alkaline-phosphatase conjugated anti-fluorescein antibody (Amersham) and a horse-peroxidase conjugated anti-digoxigenin antibody were used in combination with fast-red and tyramide fluorogenic substrates (Boehringer Mannheim and New England Nuclear).

These experiments demonstrate that $G\alpha_{14}$ is specifically and selectively expressed in circumvallate, foliate and fungiform taste receptor cells of the tongue, as shown by in situ hybridization. Therefore, $G\alpha_{14}$ is a G alpha subunit that is specifically expressed in taste receptor cells. Furthermore, this gene is co-expressed with both GPCR-B3 and GPCR-B4 receptors in the different taste papillae (see U.S. Ser. No. 09/361,652, filed Jul. 27, 1999 and U.S. Ser. No. 09/361,631, filed Jul. 27, 1999), now U.S. Pat. No. 6,383,778). Exemplary polynucleotide sequences encoding rat, mouse, and human GPCR-B3 are presented in SEQ ID NOs:3-5, respectively, encoding polypeptides having the amino acid sequences of SEQ ID NOs:6-8. Exemplary polynucleotide sequences encoding rat, mouse, and human GPCR-B4 are presented in SEQ ID NQs:9-11, respectively, encoding polypeptides having the amino acid sequences of SEQ ID NOs:12-14.

Example II

Expression of TC-Gα in a Heterologous Cell with a Taste Cell Specific G-Protein Coupled Receptor TC-Gα14 is expressed in a heterologous cell with a taste cell specific G-protein coupled receptor such as GPCR-B3 or GPCR-B4 to screen for activators, inhibitors, and modulators of TC-Gα14. Modulation of taste transduction is assayed by measuring changes in intracellular $Ca^{2+}$ levels, which change in response to modulation of the TC-Gα14 signal transduction pathway via administration of a molecule that associates with TC-Gα14. Changes in $Ca^{2+}$ levels are preferably measured using fluorescent $Ca^{2+}$ indicator dyes and fluorometric imaging. The amount of $[Ca^{2+}]_i$ is then compared to the amount of $[Ca^{2+}]_i$ in either the same cell in the absence of the test compound, or it may be compared to the amount of $[Ca^{2+}]_i$ in a substantially identical cell that lacks TC-Gα14.

---

What is claimed is:

1. A method for identifying a compound that modulates signal transduction in taste cells, the method comprising the steps of:
   (i) contacting the compound with a taste cell that expresses a G-protein alpha subunit polypeptide, wherein the G-protein alpha subunit polypeptide comprises the sequence of SEQ ID NO:2, and a taste cell specific G-protein coupled receptor (GPCR); and comprising the amino acid sequence selected from the group consisting of SEQ ID NOs: 12, 13, and 14
   (ii) determining a functional effect of the compound upon the G-protein alpha subunit polypeptide, thereby identifying a compound that modulates signal transduction in taste cells.

2. The method of claim 1, wherein the fuictional effect is a chemical effect.

3. The method of claim 1, wherein the functional effect is a physical effect.

4. The method of claim 1, wherein the functional effect is measured by determining changes in the electrical activity of cells expressing the G-protein alpha subunit polypeptide.

5. The method of claim 4, wherein the changes in electrical activity are measured by an assay selected from the group consisting of a voltage clamp assay, a patch clamp assay, a radio labeled ion flux assay, or a fluorescence assay using voltage sensitive dyes.

6. The method of claim 1, wherein the functional effect is determined by measuring changes in intracellular cyclic AMP (cAMP), cyclic GMP (cGMP), inositol triphosphate ($IP_3$), diacyl glycerol (DAG), or $Ca^{2+}$.

7. The method of claim 6, wherein the changes in intracellular cAMP or cGMP are measured using immunoassays.

8. The method of claim 1, wherein the cell or cell membrane is attached to a solid substrate.

9. The method of claim 1, wherein the cell is a eukaryotic cell.

10. The method of claim 9, wherein the cell is a human cell.

11. The method of claim 10, wherein the cell is an HEK 293 cell.

12. The method of claim 1, wherein the G-protein alpha subunit polypeptide is linked to a solid phase.

13. The method of claim 12, wherein the G-protein alpha subunit polypeptide is covalently linked to the solid phase.

* * * * *

SEQUENCE LISTING

<160> NUMBER OF SEQ ID NOS: 2

<210> SEQ ID NO 1
<211> LENGTH: 1503
<212> TYPE: DNA
<213> ORGANISM: Mus sp.
<220> FEATURE:
<221> NAME/KEY: CDS
<222> LOCATION: (157)..(1224)
<223> OTHER INFORMATION: mouse taste cell specific G-protein alpha 14
      subunit (TC-Galpha14)

<400> SEQUENCE: 1

```
aactgccttc gagaagcgtt agcctagaga tccgagcctc ttctccatac catagttggt        60
tcaggtggtt tcctcttcaa accttgcgtc tgcggataat ccgcgcggcc gggcgttaag       120
ctccaggtcc ctgtcgctcc gtcgaggtgg caagcc atg gcc ggc tgc tgc tgt        174
                                        Met Ala Gly Cys Cys Cys
                                          1               5 ttg tct gcg gag gag aaa gag tct cag cgc atc agc gcg gag atc gag        222
Leu Ser Ala Glu Glu Lys Glu Ser Gln Arg Ile Ser Ala Glu Ile Glu
         10                  15                  20 cgg cac gtt cgc cgc gac aag aag gac gcg cgc cgg gag ctc aag ctg        270
Arg His Val Arg Arg Asp Lys Lys Asp Ala Arg Arg Glu Leu Lys Leu
     25                  30                  35 ctg ttg ctg gga acc ggt gag agt ggg aaa agc acc ttt atc aag cag        318
Leu Leu Leu Gly Thr Gly Glu Ser Gly Lys Ser Thr Phe Ile Lys Gln
 40                  45                  50
```

```
                                                                      -continued atg agg ata atc cat ggg tct ggc tac agt gat gaa gat aga aag ggc       366
Met Arg Ile Ile His Gly Ser Gly Tyr Ser Asp Glu Asp Arg Lys Gly
 55                  60                  65                  70 ttc acg aag ctg gtt tac caa aac ata ttc acg gcc atg caa gcc atg       414
Phe Thr Lys Leu Val Tyr Gln Asn Ile Phe Thr Ala Met Gln Ala Met
                 75                  80                  85 atc aga gca atg gat acc ctg agg ata caa tac atg tgt gag cag aat       462
Ile Arg Ala Met Asp Thr Leu Arg Ile Gln Tyr Met Cys Glu Gln Asn
             90                  95                 100 aag gaa aat gcc cag atc atc agg gaa gtg gaa gta gac aag gtc act       510
Lys Glu Asn Ala Gln Ile Ile Arg Glu Val Glu Val Asp Lys Val Thr
        105                 110                 115 gca ctc tct aga gac cag gtg gca gcc atc aag cag ctg tgg ctg gat       558
Ala Leu Ser Arg Asp Gln Val Ala Ala Ile Lys Gln Leu Trp Leu Asp
    120                 125                 130 ccc gga atc cag gag tgt tac gac agg agg agg gag tac cag ctg tca       606
Pro Gly Ile Gln Glu Cys Tyr Asp Arg Arg Arg Glu Tyr Gln Leu Ser
135                 140                 145                 150 gac tct gcc aaa tat tac ctg acg gac att gag cgt atc gcc atg ccc       654
Asp Ser Ala Lys Tyr Tyr Leu Thr Asp Ile Glu Arg Ile Ala Met Pro
                155                 160                 165 tct ttc gtg cca aca caa cag gat gtg ctt cgt gtt aga gtg ccc acc       702
Ser Phe Val Pro Thr Gln Gln Asp Val Leu Arg Val Arg Val Pro Thr
            170                 175                 180 act ggc atc ata gaa tat cca ttc gac ctg gaa aac atc atc ttc cga       750
Thr Gly Ile Ile Glu Tyr Pro Phe Asp Leu Glu Asn Ile Ile Phe Arg
        185                 190                 195 atg gtg gat gtt ggt ggc cag cga tct gaa cga cgg aaa tgg att cac       798
Met Val Asp Val Gly Gly Gln Arg Ser Glu Arg Arg Lys Trp Ile His
    200                 205                 210 tgc ttt gag agt gtc acc tcc atc att ttc ttg gtt gct ctg agt gaa       846
Cys Phe Glu Ser Val Thr Ser Ile Ile Phe Leu Val Ala Leu Ser Glu
215                 220                 225                 230 tat gac cag gtt ctg gct gag tgt gac aat gag aac cgc atg gag gag       894
Tyr Asp Gln Val Leu Ala Glu Cys Asp Asn Glu Asn Arg Met Glu Glu
                235                 240                 245 agc aaa gcc ctg ttt aga acc atc atc acc tac ccc tgg ttt ctg aac       942
Ser Lys Ala Leu Phe Arg Thr Ile Ile Thr Tyr Pro Trp Phe Leu Asn
            250                 255                 260 tcc tcc gtg att ctg ttc tta aac aag aag gat ctt cta gag gag aaa       990
Ser Ser Val Ile Leu Phe Leu Asn Lys Lys Asp Leu Leu Glu Glu Lys
        265                 270                 275 atc atg tac tct cat cta att agc tac ttc cca gag tac aca gga cca      1038
Ile Met Tyr Ser His Leu Ile Ser Tyr Phe Pro Glu Tyr Thr Gly Pro
    280                 285                 290 aag caa gat gtc aaa gcg gcc agg gac ttt atc ctg aag ctg tat caa      1086
Lys Gln Asp Val Lys Ala Ala Arg Asp Phe Ile Leu Lys Leu Tyr Gln
295                 300                 305                 310 gac cag aat cct gac aaa gag aag gtt atc tat tct cac ttc act tgt      1134
Asp Gln Asn Pro Asp Lys Glu Lys Val Ile Tyr Ser His Phe Thr Cys
                315                 320                 325 gct aca gac acc gag aat atc cgc ttt gtg ttt gct gct gtc aaa gac      1182
Ala Thr Asp Thr Glu Asn Ile Arg Phe Val Phe Ala Ala Val Lys Asp
            330                 335                 340 aca atc cta cag cta aac cta cgg gag ttc aac ttg gtg taa              1224
Thr Ile Leu Gln Leu Asn Leu Arg Glu Phe Asn Leu Val
        345                 350                 355 atggagggcc tactcctccg agacagaggg tgatctgagc ccttcctgcc tgatctacaa    1284
gtgcttctgg accaggacct aaggacatta tgtagcccac aggacagaga tgggtagtgc   1344
```

```
aatgtgaaaa atacttcacc aacccttttta agtgtctttta attcttcact gtctaactct    1404
tttctcgcct tttggttgaa cgattaggta tcattttga gtggttcccc ctctcctatt     1464
tttttaaact agtgttcaac agttattaaa aaatcatgc                            1503
```

<210> SEQ ID NO 2
<211> LENGTH: 355
<212> TYPE: PRT
<213> ORGANISM: Mus sp.

<400> SEQUENCE: 2

```
Met Ala Gly Cys Cys Leu Ser Ala Glu Glu Lys Glu Ser Gln Arg
 1               5                  10                  15

Ile Ser Ala Glu Ile Glu Arg His Val Arg Arg Asp Lys Lys Asp Ala
            20                  25                  30

Arg Arg Glu Leu Lys Leu Leu Leu Gly Thr Gly Glu Ser Gly Lys
        35                  40                  45

Ser Thr Phe Ile Lys Gln Met Arg Ile Ile His Gly Ser Gly Tyr Ser
    50                  55                  60

Asp Glu Asp Arg Lys Gly Phe Thr Lys Leu Val Tyr Gln Asn Ile Phe
65                  70                  75                  80

Thr Ala Met Gln Ala Met Ile Arg Ala Met Asp Thr Leu Arg Ile Gln
                85                  90                  95

Tyr Met Cys Glu Gln Asn Lys Glu Asn Ala Gln Ile Ile Arg Glu Val
            100                 105                 110

Glu Val Asp Lys Val Thr Ala Leu Ser Arg Asp Gln Val Ala Ala Ile
        115                 120                 125

Lys Gln Leu Trp Leu Asp Pro Gly Ile Gln Glu Cys Tyr Asp Arg Arg
    130                 135                 140

Arg Glu Tyr Gln Leu Ser Asp Ser Ala Lys Tyr Tyr Leu Thr Asp Ile
145                 150                 155                 160

Glu Arg Ile Ala Met Pro Ser Phe Val Pro Thr Gln Gln Asp Val Leu
                165                 170                 175

Arg Val Arg Val Pro Thr Thr Gly Ile Ile Glu Tyr Pro Phe Asp Leu
            180                 185                 190

Glu Asn Ile Ile Phe Arg Met Val Asp Val Gly Gly Gln Arg Ser Glu
        195                 200                 205

Arg Arg Lys Trp Ile His Cys Phe Glu Ser Val Thr Ser Ile Ile Phe
    210                 215                 220

Leu Val Ala Leu Ser Glu Tyr Asp Gln Val Leu Ala Glu Cys Asp Asn
225                 230                 235                 240

Glu Asn Arg Met Glu Glu Ser Lys Ala Leu Phe Arg Thr Ile Ile Thr
                245                 250                 255

Tyr Pro Trp Phe Leu Asn Ser Ser Val Ile Leu Phe Leu Asn Lys Lys
            260                 265                 270

Asp Leu Leu Glu Glu Lys Ile Met Tyr Ser His Leu Ile Ser Tyr Phe
        275                 280                 285

Pro Glu Tyr Thr Gly Pro Lys Gln Asp Val Lys Ala Ala Arg Asp Phe
    290                 295                 300

Ile Leu Lys Leu Tyr Gln Asp Gln Asn Pro Asp Lys Glu Lys Val Ile
305                 310                 315                 320

Tyr Ser His Phe Thr Cys Ala Thr Asp Thr Glu Asn Ile Arg Phe Val
                325                 330                 335
```

```
Phe Ala Ala Val Lys Asp Thr Ile Leu Gln Leu Asn Leu Arg Glu Phe
            340                 345                 350
Asn Leu Val
        355
```